US008432944B2

(12) United States Patent  
Romanovsky et al.

(10) Patent No.: US 8,432,944 B2  
(45) Date of Patent: Apr. 30, 2013

(54) EXTENDING THE LIFETIME OF A DEEP UV LASER IN A WAFER INSPECTION TOOL

(75) Inventors: Anatoly Romanovsky, Palo Alto, CA (US); George Kren, Los Alto Hills, CA (US); Bret Whiteside, Gilroy, CA (US)

(73) Assignee: KLA-Technor Corporation, Milpitas, CA (US)

( * ) Notice: Subject to any disclaimer, the term of this patent is extended or adjusted under 35 U.S.C. 154(b) by 106 days.

(21) Appl. No.: 13/153,942

(22) Filed: Jun. 6, 2011

(65) Prior Publication Data

US 2011/0315897 A1 Dec. 29, 2011

Related U.S. Application Data

(60) Provisional application No. 61/384,795, filed on Sep. 21, 2010, provisional application No. 61/358,873, filed on Jun. 25, 2010.

(51) Int. Cl.
*H01S 3/13* (2006.01)

(52) U.S. Cl.
USPC .............. 372/29.021; 372/29.02; 372/20; 372/21; 372/24; 372/41; 359/837; 359/831

(58) Field of Classification Search ............. 372/29.021, 372/20.02, 20, 21, 24, 41; 359/837, 831
See application file for complete search history.

(56) References Cited

U.S. PATENT DOCUMENTS

| 5,134,298 | A | 7/1992 | Inagaki |
| 7,388,172 | B2 * | 6/2008 | Sercel et al. ............. 219/121.72 |
| 2004/0130689 | A1 * | 7/2004 | Starikov et al. ................. 355/53 |
| 2005/0225732 | A1 * | 10/2005 | Conner et al. ................... 353/31 |
| 2006/0148210 | A1 | 7/2006 | Furuta |
| 2007/0072099 | A1 | 3/2007 | Sullivan |
| 2009/0218488 | A1 | 9/2009 | Wells |
| 2011/0051760 | A1 | 3/2011 | Dunstan |

FOREIGN PATENT DOCUMENTS

EP 2388800 A1 11/2011

OTHER PUBLICATIONS

Use of Laser Diode in Joint Transform Correlator; Opt. Eng. 43, 1751 (2004).

* cited by examiner

*Primary Examiner* — Kinam Park  
(74) *Attorney, Agent, or Firm* — Deborah Wenocurkla

(57) ABSTRACT

Disclosed herein is a method and apparatus for automatic correction of beam waist position drift in real time, using wafer inspection data taken during normal tool operation. Also disclosed herein is an improved laser astigmatism corrector for use either internal or external to the laser.

8 Claims, 10 Drawing Sheets

Gaussian beam width $w(z)$ as a function of the axial distance $z$.
$w_0$: beam waist;
$b$: depth of focus;
$z_R$: Rayleigh range;
$\Theta$: total angular spread The beam waist (or *beam focus*) is the location along the propagation direction where the beam radius has a minimum.

EXTENDING THE LIFETIME OF A DEEP UV LASER IN A WAFER INSPECTION TOOL

CROSS REFERENCE TO RELATED APPLICATIONS

This application is related to U.S. Provisional application No. 61/358,873 filed Jun. 25, 2010, and also to U.S. Provisional application No. 61/384,795, filed Sep. 21, 2010, and claims priority to both of the aforementioned provisional applications.

FIELD OF THE INVENTION

This invention is in the field of integrated circuit processing, and in particular in the field of wafer inspection systems.

BACKGROUND

Wafer inspection systems, and in particular unpatterned wafer inspection systems such as the Surfscan tool made by KLA-Tencor, utilize a laser light source with a beam directed at a wafer. FIG. 1a illustrates a portion of the wafer inspection system 100, including light from the light source impinging on the wafer. The beam 102 emerging from the laser source 105 travels through beam forming optics 110 and focusing elements 115 before arriving at the wafer 120. The incident light impinges on wafer 120 with a spot size 126. Wafer 120 is positioned on wafer chuck 122 on stage 124.

The wafer inspection system may also include Scattered Light Collection Optics (SLCO) 128, a photodetector (also called photosensor) 135, and a digitizer 137. These function to collect scattered light from the wafer surface and local point defects on the wafer, and convert it to a digital electrical signal that can be than transferred to an Image/Data processing Computer 140 (which will be referred to hereinafter as an IMC)

Scattered light 130 is collected by the SLCO and converted to a digital electrical signal by one or more sensors 135 which may be a photodetector 135, combined with a digitizer 137. IMC 140 which may include a controller 142 for the stage 124 and optics 110, analyzes the signal from sensors 135.

Wafer inspection systems can utilize various types of wafer scanning. The scan speed and spot size are related to the required sampling times according to the scan type.
1. XY Raster Scan utilizes a stationary incident beam, while the wafer translates in x and y directions to generate a raster scan of the wafer. During the raster scan samples of scattered light are collected by the digitizer and transferred to the IMC for analysis. The required sampling time intervals in the X and Y directions are at least 2XSpotsize/XBeam speed, and at least 2YSpotsize/2YbeamSpeed. The pitch of the scan in the rastering direction, which will be designated as the Y-direction, should be at least half the Y spot size. For the purposes of this disclosure, the spot size is defined as the size of the illuminated portion of the wafer where the light power density of every point is greater than $1/e^2$ of the maximum spot power density.
2. R-Theta Spiral Scan utilizes a stationary Incident Beam while the wafer translates in R and rotates in Theta directions to generate a Spiral scan of the wafer. During the spiral scan, samples of scattered light are collected by the digitizer and transferred to the IMC for analysis. The required sampling time intervals in the R and Theta directions are at least 2XSpotsize/ThetaBeam speed, and at least 2YSpotsize/2RbeamSpeed. The R pitch of spiral scan should be at least ½ of the Y spot size.

3. More complex wafer scans are also possible where the wafer and beam are both moving. The principles of this invention can also be used for complex wafer scans.

FIG. 1b is an enlarged illustration of an embodiment of a deep UV laser source which may comprise the laser source portion of the system. The Deep UV (DUV) laser 142 may include:

Green laser 145 which generates the primary laser beam. The green wavelength may fall between 514 and 570 nm, depending on the method and material used to generate it;

Non-linear crystal 150 which acts as a frequency doubler, to yield a DUV laser beam 152. The UV wavelength is accordingly half the wavelength of the green laser, with wavelength in the range between 257-285 nm. Examples of types of non-linear crystals include but are not limited to Beta Barium Borate (BBO) and Cesium Lithium Borate (CLBO). Spot changer stage 155 may be included to adjust the position of crystal 150.

The focusing elements shape the beam to narrow down to beam waist 125. FIG. 1c shows an enlargement of the beam waist, and indicates parameters such as depth of focus and angular spread which characterize the beam waist profile. The beam waist is positioned at a Z position where the XY cross-section of the beam width is minimized. (please note that for the purposes of this invention, the Z axis is defined as shown in this figure). This Z position of the beam waist may occur at a different Z value if the beam minimum radius measured along the X axis occurs at a different Z from the minimum radius measured along the Y axis. These two values are described as the X and Y beam waist positions respectively. If the beam waist is positioned at wafer surface 120, optimal focus is achieved. In order to have repeatable and sensitive measurement, beam 102 needs to be focused on wafer 120. It is critical that the front wafer surface is located at the focus of the incident beam in both X and Y dimensions, i.e., that the X and Y beam waists are in the same plane as the front wafer surface plane. There are several possible reasons that the X and/or Y beam waists may not be in the same plane as the front wafer surface plane:

1. The X and Y beam waist positions are uniformly displaced from the initial system alignment condition, either because the wafer moved in Z from the initial system alignment condition, or because the X and Y beam waists uniformly changed their position relative to the initial system alignment. In these cases the laser beam is not astigmatic.
2. The X and Y beam waist positions are displaced relative to one another, which may be due to frequency doubling non linear crystal aging. In this case astigmatism exists in the laser beam. Astigmatism is shown pictorially in FIG. 1d.

Note that there is generally some initial astigmatism (which is minimized as much as possible) in a newly built and aligned calibrated system which can be tolerated according to system performance margins that take the initial astigmatism into account. An important factor contributing to astigmatism increase is the aging of the non-linear crystal, as will be described hereinafter. This factor can induce astigmatism to the point where at least one of the spot sizes (X or Y) is much larger than what was intended.

It is a known problem that for a DUV laser with wavelength shorter than around 200-285 mm, as used in the Wafer Inspection tool, the laser non linear crystal which is used as a frequency doubler has a limited life. (Note that the type of laser and laser crystal described herein is one example, but that this is a general phenomenon for crystal based lasers, and the details thereof depend on power density, wavelength, and type of crystal). Degradation of the crystals in the DUV laser case is thought to be caused by the high photon energies at these wavelengths.

As the laser crystal ages and degrades, the beam waist position can drift, and x- and y-beam waist positions can drift at different rates, causing a drift in astigmatism and also increasing the illumination spot size on the wafer. This will adversely affect measurement accuracy and sensitivity. The response, i.e., the scattering signal from a defect of interest will change (instability), and will be reduced (loss of sensitivity). Correction of this instability when defocusing reaches a certain limit requires frequent and costly servicing of the tool, calibrations, realignment, spot size change, switching the frequency doubler laser spot where the laser light impinges on the crystal (the crystal is generally significantly larger than the laser beam), i.e. rotating or otherwise moving the crystal, or early replacement of lasers. All of these correction methods are costly and time-consuming.

SUMMARY

Disclosed herein is a method and apparatus for automatic correction of beam waist position drift in real time, using wafer inspection data taken during normal tool operation.

Also disclosed herein is an improved laser astigmatism corrector for use either internal or external to the laser.

BRIEF DESCRIPTION OF THE DRAWINGS

FIG. 3b is a continuation of the flow chart of FIG. 3a.

DETAILED DESCRIPTION

The current practice for correction of beam waist position drift and astigmatism drift is to recalibrate the tool, in the case when beam waist position changes in X and in Y by the same amount (i.e., without astigmatism). Astigmatism is generally dealt with by assuming a fixed lifetime for each spot on the frequency doubler crystal, which is generally shorter than the actual lifetime of a particular spot. Periodic maintenance is usually prescribed, to move the frequency doubler crystal so as to expose a new spot. This method is problematic. Each time the spot is changed, verification of tool performance and recalibration of the tool is required. Also, since the periodic maintenance must be scheduled at shorter intervals than the actual spot lifetime, and due to the limited number of available spots on the crystal, this method results in premature changing of the very expensive laser crystal. Customer tool down time adds to the high cost.

The standard methods for correction of beam waist position drift and astigmatism drift, as described above, are time consuming and costly, significantly increasing the cost of ownership of a wafer inspection tool. Disclosed herein are apparatus and methods of automatic astigmatism and waist position correction which utilize measurements taken during normal tool operation, i.e. which utilize wafer inspection data. This information is used as feedback for correction of astigmatism and beam waist drift. Mechanisms are employed to compensate for the measured drift with a slow servo control loop The servo loop does not need to be fast because beam waist drift and astigmatism drift are relatively slow processes. Therefore beam waist and astigmatism corrections can happen in small increments between wafer scans, therefore it does not reduce throughput of the tool and does not introduce any additional instability of measurement.

An embodiment of an inventive apparatus adds a Z-stage to wafer chuck 122, and further includes an astigmatism compensation device or astigmatism corrector either internal to the laser source 105, or near to but external to laser source 105, and a means for measuring spot defocusing in the X and Y beam directions. Defocus is determined by comparing the spot size to reference spot sizes as will be described hereinafter.

Figure 1A:
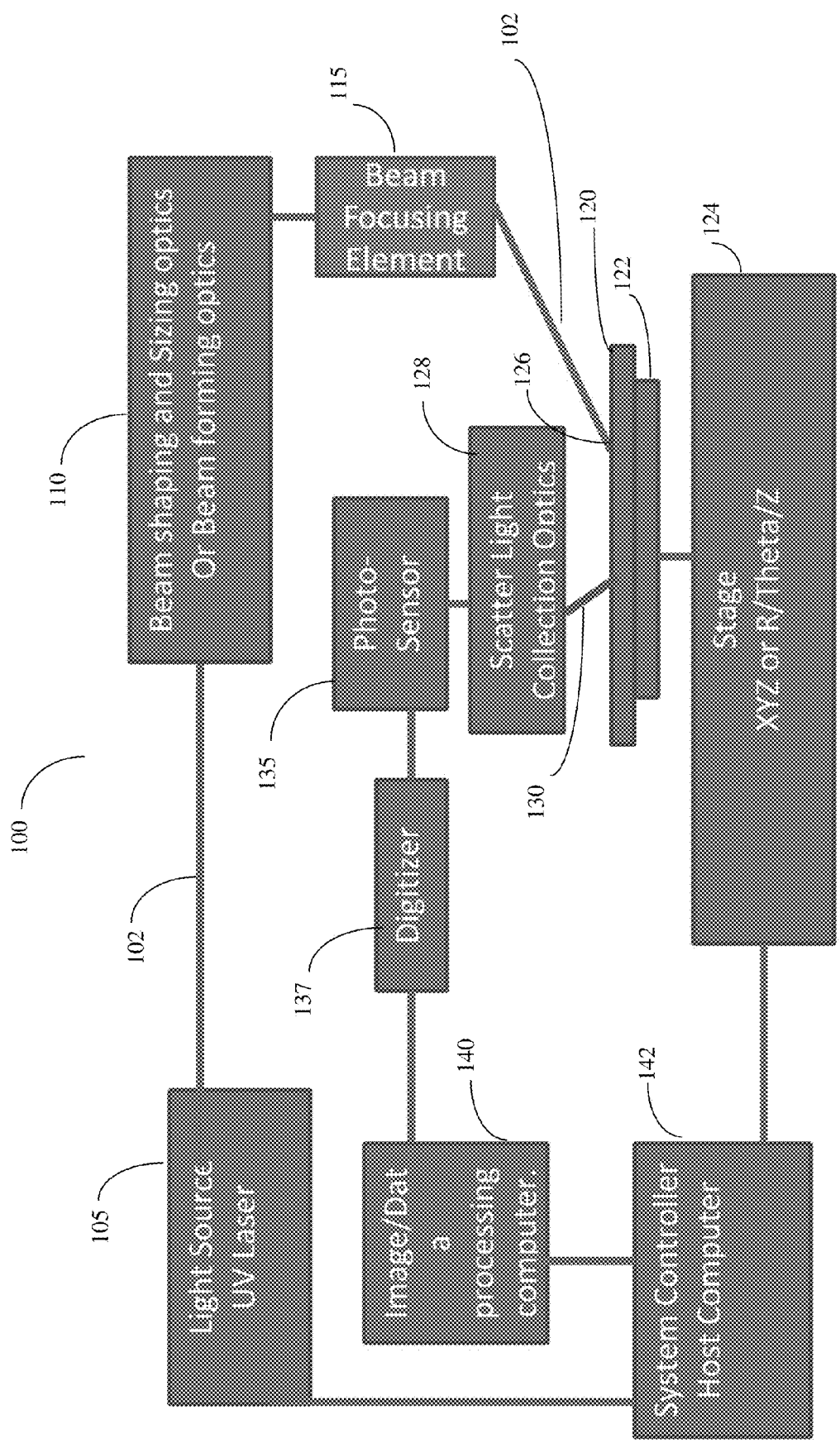
FIG. 1a illustrates a portion of a wafer inspection system, including light from the light source impinging on the wafer.
Figure 1B:
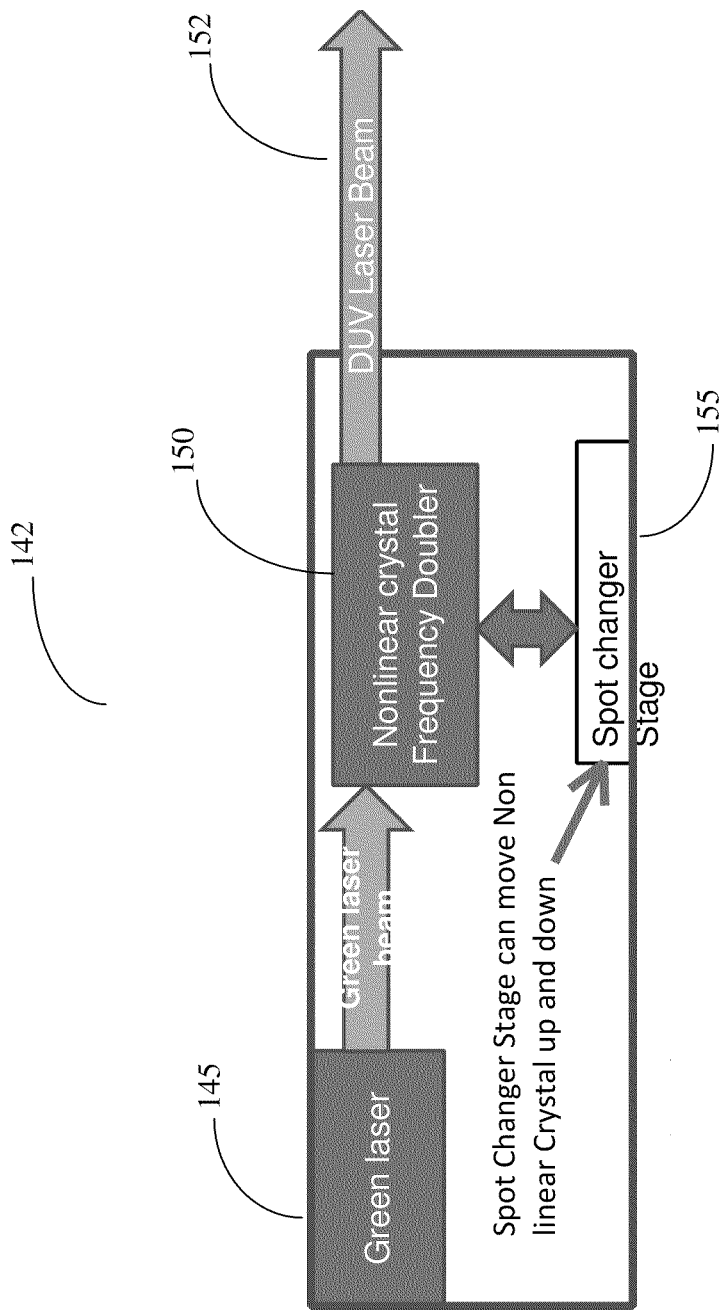
FIG. 1b is an enlarged illustration of an embodiment of a deep UV laser source.
Figure 1C:
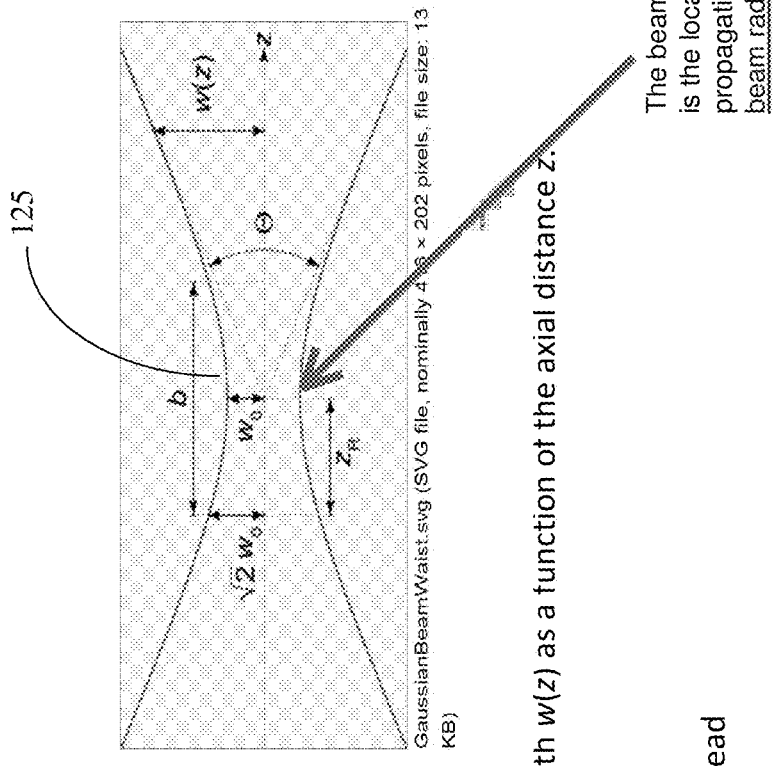
FIG. 1c shows an enlargement of the beam waist.
Figure 1D:
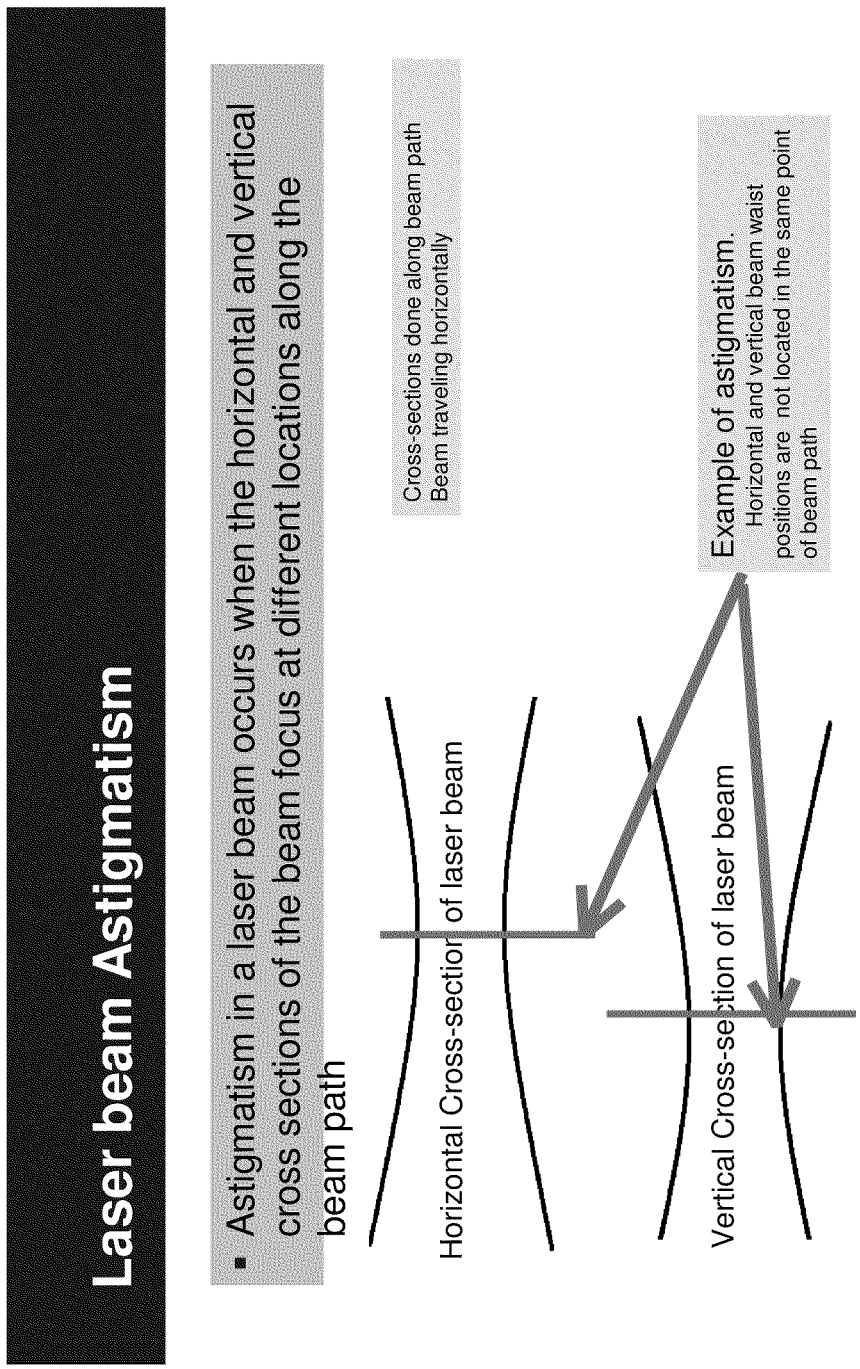
FIG. 1d pictorially illustrates astigmatism.
Figure 2:
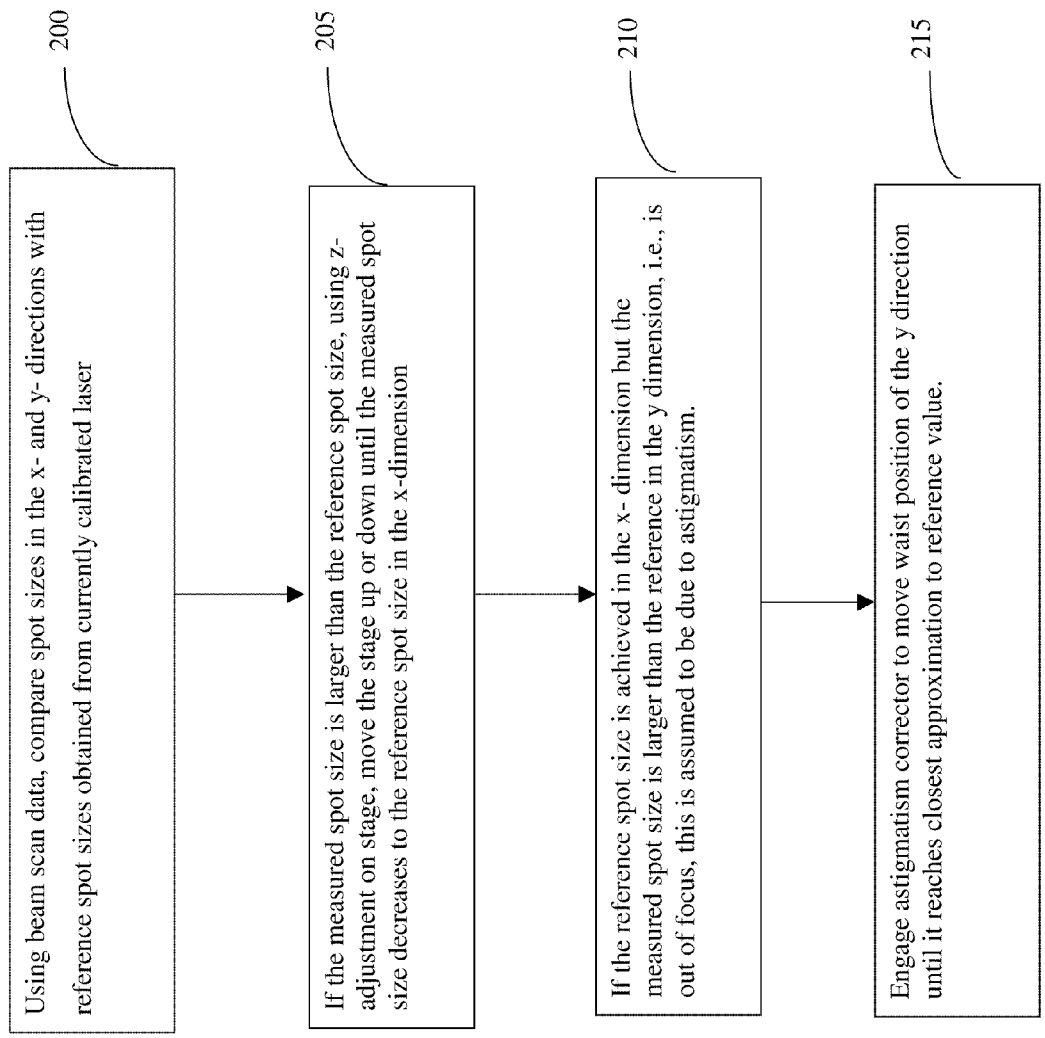
FIG. 2 illustrates a high level flow diagram describing an embodiment of the method of beam waist and astigmatism drift correction.

FIG. 2 illustrates a high level flow diagram describing an embodiment of the method of beam waist and astigmatism drift correction. Note that this correction algorithm is exemplary and not limiting.

In step 200, using beam scan data, compare spot sizes in the x- and y-directions with reference spot sizes which may be obtained from a currently calibrated laser, and defined according to the acceptable spot size range for proper operation of the tool.

In step 205, if the measured spot size is larger than the reference spot size, using z-adjustment on stage, move the stage up or down until the measured spot size decreases to the reference spot size in the x direction as defined below. For the purposes of this illustration, we will define that the x direction is aligned with the axis that has the more stable beam waist position, and is therefore adjusted with the z stage. If the measured spot size remains larger than the reference spot size after both up and down z-adjustment, realignment, recalibration, or replacement of the laser crystal is required.

In step 210, if the reference spot size is achieved in the x-direction (as defined above), but the measured spot size is larger than the reference in the y direction, i.e., is out of focus, this is assumed to be due to astigmatism.

In step 215, engage astigmatism corrector to move waist position of the y direction until it reaches closest approximation to reference value.

Referring now to step 200:

During wafer scan, scattered light is detected from defects on the wafer surface. In general, these defects are significantly smaller in diameter than the diameter of the laser beam, with a sampling distance smaller than the spot size. The spiral or raster scan type scanning scheme results in measurement of the laser beam intensity in both the x- and y-dimension, as provided by photodetector (or other sensor) signal. These incoming intensity signals are analyzed by computer 140, which calculates x- and y-Gaussian intensity profiles, and calculates spot size in the x- and y-direction. Stored in the computer are reference spot sizes in the x- and y-directions, which may have been obtained and stored during system calibration.

Figure 3A:
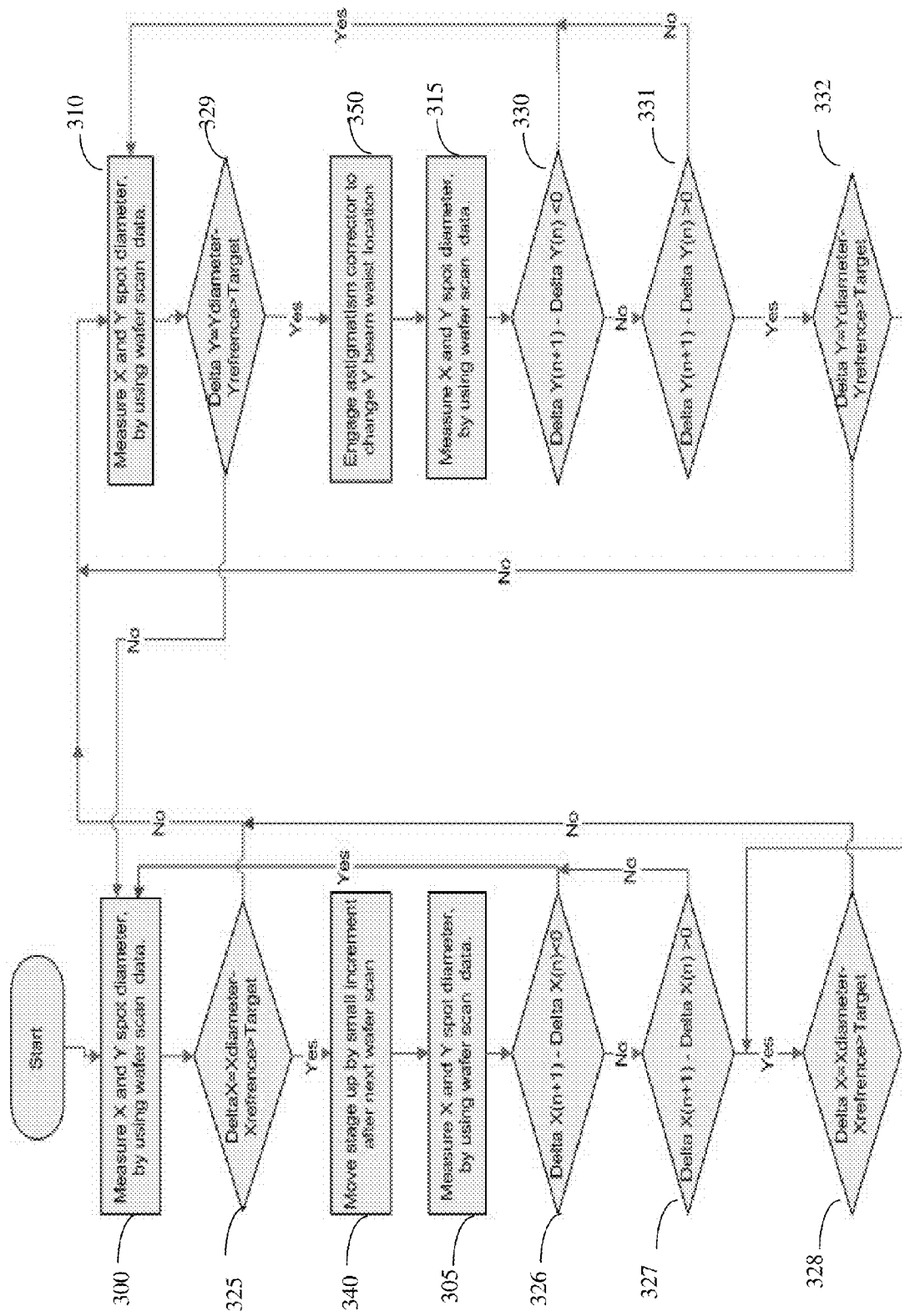
FIG. 3a is a flow chart which describes in more detail an embodiment of the control loop decisions of the computer controller according to an exemplary algorithm.
Figure 3B:
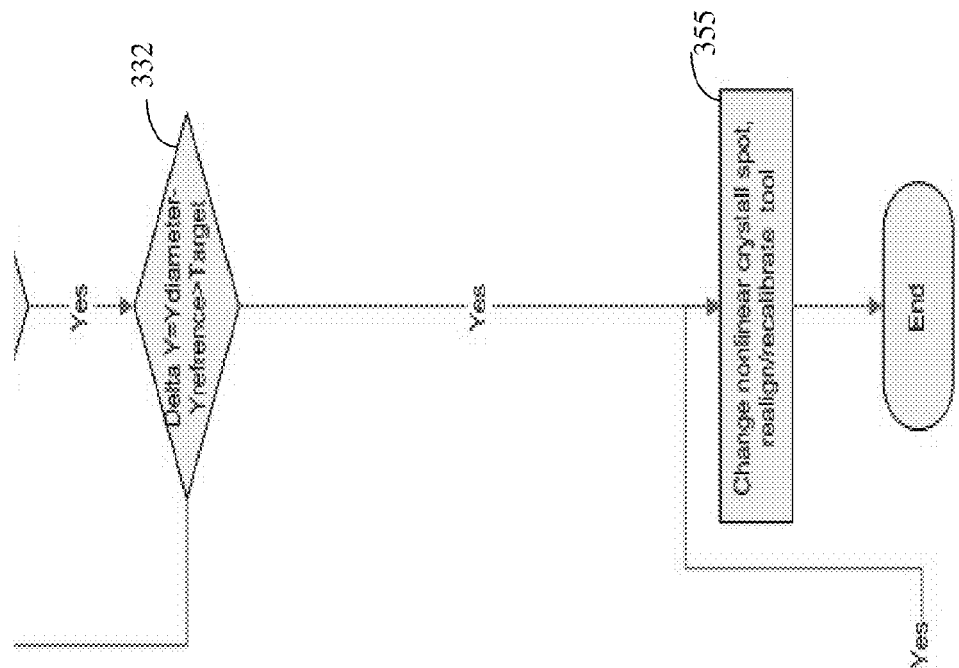

FIG. 3a is the beginning of a flow chart which describes in more detail the decisions of the computer controller in the algorithm embodiment which is outlined in steps 205-215 above. Note that this algorithm is exemplary and not limiting. The flow chart is continued in FIG. 3b.

Steps 300,305,310,315,320 comprise measuring x and y spot diameter, using wafer scan data. Note that the beam waist occurs at the minimum spot diameter position, so measurement of spot diameter is connected to beam waist position. Steps 325-334 comprise determining the delta between the current spot diameters and previous or reference spot diameters. Steps 340,345 comprise moving the stage up or down to move the beam waist position for coarse correction in the x-direction (followed by re-measuring of spot diameters to determine if the z-movement was moving the spot size towards the reference, or focused, size). Step 350 comprises engaging the astigmatism corrector to move the beam waist position for fine correction in the y-direction. Step 355 comprises changing the crystal location, realigning, or recalibrating the tool, in the event that the z-stage movement is unable to correct for the less sensitive beam waist drift in the x-direction.

Figure 4A:
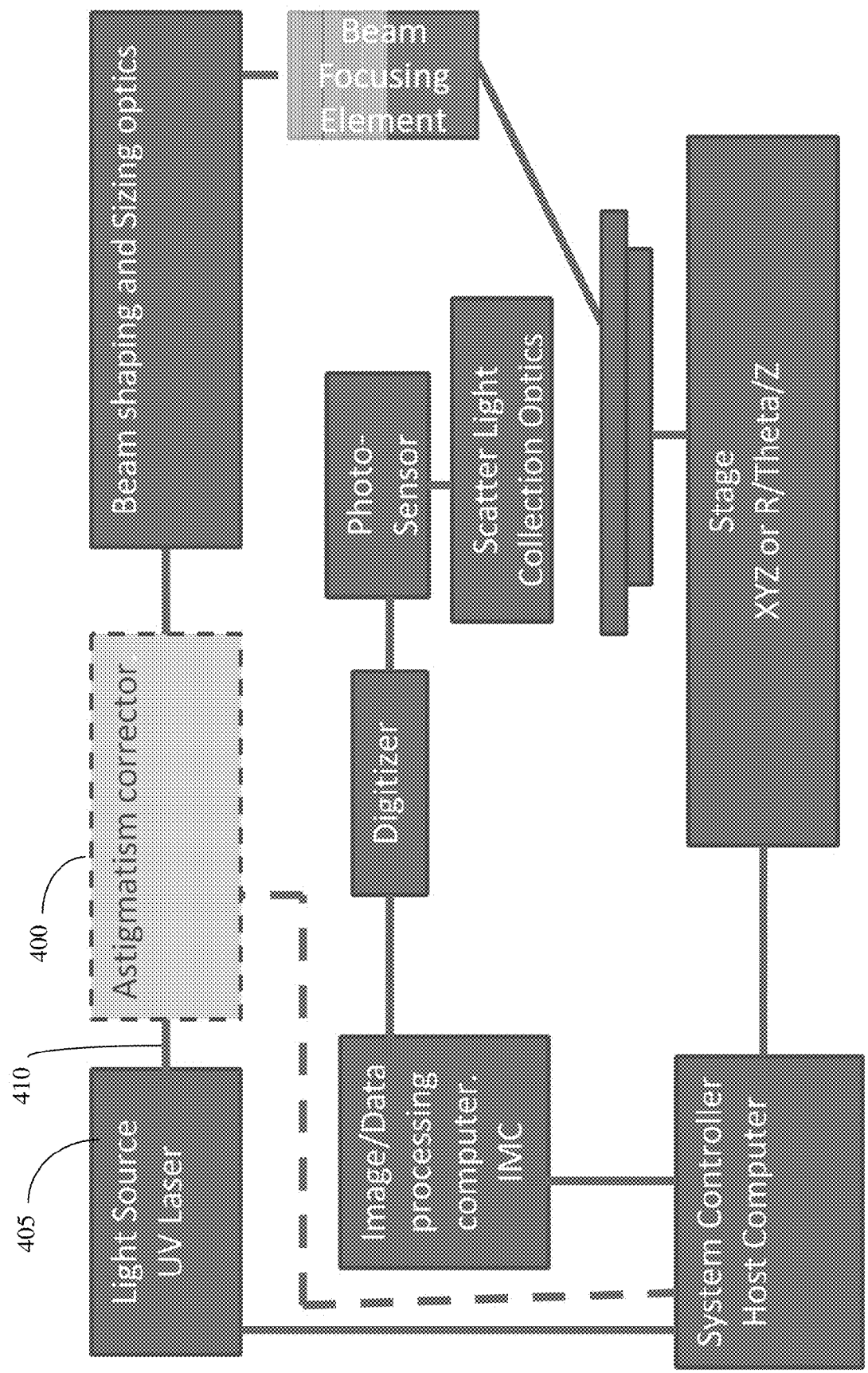
FIG. 4a illustrates a first exemplary embodiment of an inventive laser astigmatism corrector layout which could be used in the above described process flow.
Figure 4B:
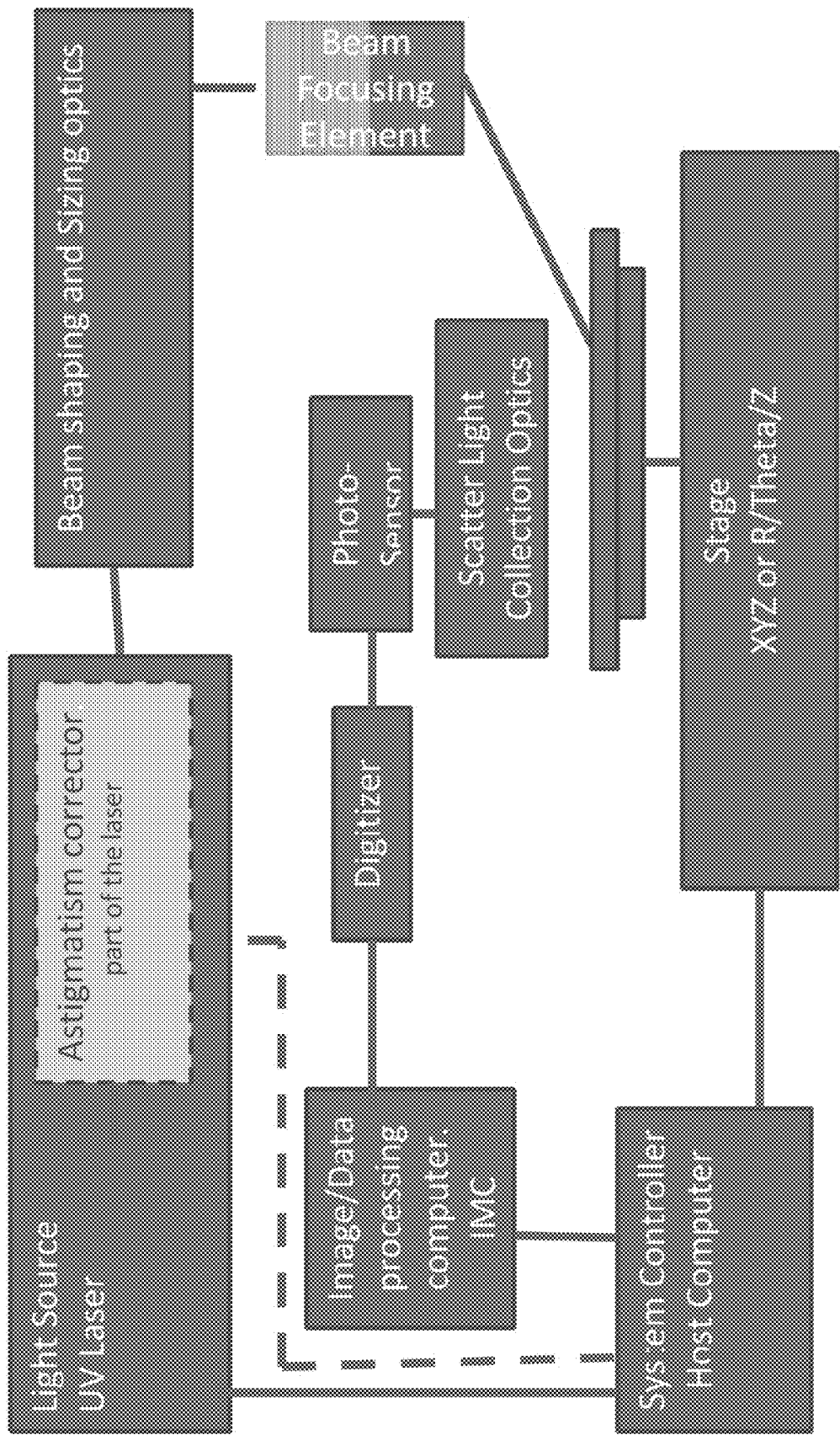
FIG. 4b illustrates a second exemplary embodiment of a laser astigmatism corrector layout which could be used in the above described process flow.

FIG. 4a illustrates a first exemplary embodiment of a laser astigmatism corrector layout which could be used in the above described process flow. Note that this embodiment is exemplary but not limiting. In this embodiment, the astigmatism corrector 400 is positioned outside the laser 405 in a system illumination path 410. Alternately, as shown in FIG. 4b, the astigmatism corrector could be implemented inside of a laser as an integral part of the laser assembly. It should also be noted that many types of astigmatism correctors could be used in this layout. A known method of laser astigmatism correction uses cylindrical mirrors. This method is described in *Use of laser diode in joint transform correlator, Opt. Eng.* 43, 1751 (2004); doi:10.1117/1.1763590. In addition to the known laser astigmatism correctors, an inventive laser astigmatism corrector is disclosed herein. Laser astigmatism corrector 400 is designed to reduce the axial astigmatism associated with harmonic generating lasers that focus the photon flux into birefringent crystals having different indices of refraction in orthogonal directions transverse to the laser propagation direction. This type of laser can have both static and dynamic astigmatism, the latter being particularly difficult to deal with when the rate of drift is fast compared to the frequency of laser preventative maintenance cycles. Therefore, an adjustable astigmatism corrector is proposed which has several advantages to a traditional cylinder lens method of correction.

Figure 5:
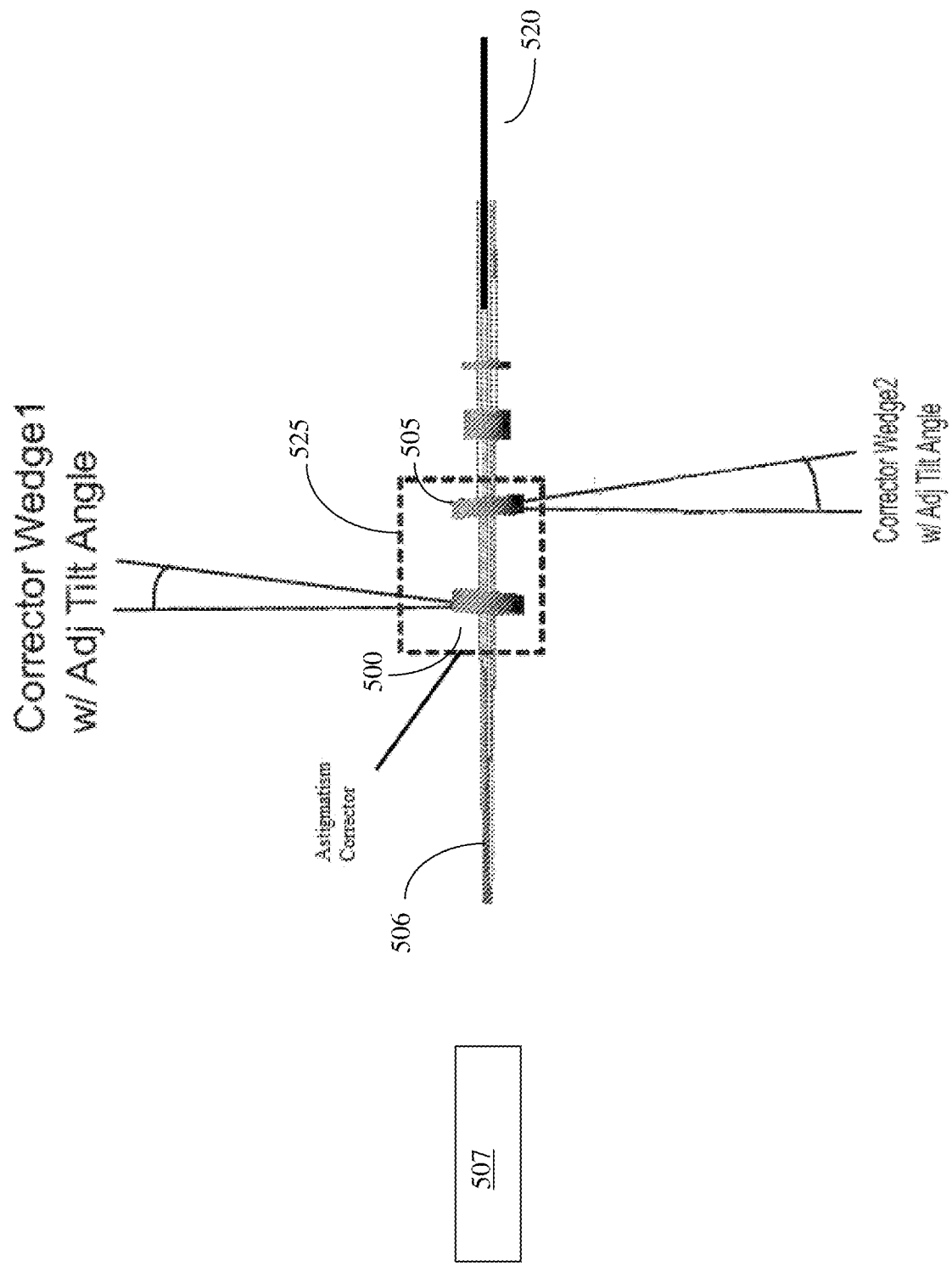
FIG. 5 illustrates an enlargement of an inventive astigmatism corrector embodiment.

FIG. 5 illustrates an embodiment of an adjustable astigmatism corrector. It is comprised of two wedged plates 500, 505 having small wedge angle such as 0.5°, 1°, or 2°. The wedges have adjustable tilt angles. The wedges are mounted in the path of beam 506 from laser 507, oriented either in the xz or the yz plane to correct the beam asymmetry between the two planes. By tilting the wedge plates relative to one of the planes, the beam divergence in that plane can be adjusted to compensate for astigmatism. The plates may be made of a very high quality transparent material such as glass, so as not to degrade the original beam quality. Both wedges can be identical and can be manufactured from the same large sheet of glass to avoid having to tilt-tune one with respect to the other. The two wedges are installed pointing in opposing directions, i.e., either one pointing up and the other pointing down, or one pointing to the left side of the beam and the other toward the right side of the beam. This opposition of wedge directions eliminates any beam pointing errors once the wedges are aligned. Each wedge is tilted in the same plane and in the same direction from its thicker end, and the two wedges are rotated by 180 degrees about the optical axis 520 with respect to each other, thus eliminating the beam offset which would be produced by either plate individually. The wedged plates 500, 505 may be configured into astigmatism corrector subassembly 525. Advantages of the inventive astigmatism corrector with respect to cylindrical lens correctors include:

1. Cylindrical lenses of sufficiently high quality are difficult to manufacture, and they require very long focal lengths to apply only a minor astigmatism correction. In contrast, the counter-tilted/counter-rotated wedges are disclosed herein are greatly adjustable and can be made with very flat surfaces that do not introduce other wavefront quality issues into the laser beam
2. The tilted waveplate design can be positioned inside of a traditional beam expander, e.g., a Keplerian telescope (shown on the figure as subassembly 525) This would allow for very thin wedges and small tilt angles, generally +/−0 to 2 degrees], making the assembly compact and able to be designed using flexures for improved stability and precision. Wedge center thickness may be in the range 1-5 mm, and, depending on the wedge diameter and included angle, the thickness variation from top to bottom may be in the range of 50 um-1 mm.
3. Multi-element waist relay-type astigmatism correctors, which typically include focusing elements of both spherical and cylindrical forms, require the knowledge of the exact x- and y-waist locations relative to a fixed reference plane, in order to determine the spacing and location of each focusing element, i.e., lens. The inventive tilted waveplate astigmatism corrector only requires knowledge of the relative distance between the x- and y-waist, which enables quick feedback.

TABLE 1

| | CORRECTOR PLATES WITH 0.5°, 1.0°, AND 2.0° WEDGES 0.5, 1.0 and 2.0 DEG WEDGED PLATES | | | | | |
|---|---|---|---|---|---|---|
| ISF | Astig @ Laser (P-V wv) | Astig @ Laser (% RR) | AST @ Wafer w/7 um Spot (um) | Tilt w/2° Wedge (deg) | Tilt w/1° Wedge (deg) | Tilt w/0.5° Wedge (deg) |
| 1 | 0.27 | 40 | 58.3 | 0.2860 | 2.0000 | 4.5067 |
| 0.9 | 0.243 | 36 | 52.4 | 0.1590 | 1.7552 | 4.0592 |
| 0.8 | 0.216 | 32 | 46.6 | 0.0340 | 1.5098 | 3.6051 |
| 0.7 | 0.189 | 28 | 40.7 | −0.0914 | 1.2635 | 3.1467 |
| 0.6 | 0.162 | 24 | 34.9 | −0.2173 | 1.0162 | 2.6812 |
| 0.5 | 0.135 | 20 | 29.1 | −0.3422 | 0.7679 | 2.2095 |
| 0.4 | 0.108 | 16 | 23.3 | −0.4689 | 0.5187 | 1.7315 |
| 0.3 | 0.081 | 12 | 17.5 | −0.5954 | 0.2686 | 1.2472 |
| 0.2 | 0.054 | 8 | 11.7 | −0.7221 | 0.0184 | 0.7566 |

TABLE 1-continued

CORRECTOR PLATES WITH 0.5°, 1.0°, AND 2.0° WEDGES
0.5, 1.0 and 2.0 DEG WEDGED PLATES

| ISF | Astig @ Laser (P-V wv) | Astig @ Laser (% RR) | AST @ Wafer w/7 um Spot (um) | Tilt w/2° Wedge (deg) | Tilt w/1° Wedge (deg) | Tilt w/0.5° Wedge (deg) |
|---|---|---|---|---|---|---|
| 0.1 | 0.027 | 4 | 5.8 | −0.8474 | −0.2343 | 0.2597 |
| 0 | 0.000 | 0 | 0 | −0.9740 | −0.4871 | −0.2436 |

Table 1 shows numerical values of astigmatism and the necessary tilt angles for different wedge angles in order to provide equal and opposite astigmatism correction. ISF (Improvement Scale Factor) is the fraction of the maximum astigmatism which is correctable for a given range of wedge tilt angles. Note that due to the nominal wedge of each plate and the fact that this embodiment places the wedges inside a beam expander where the beam is not collimated, even when the laser starts out with zero astigmatism the wedges require non-zero tilt. RR (Rayleigh Range) is the z distance to increase the laser spot size by root 2 or increase the beam area by 2× (which is half of what is known as the laser depth-of focus or the confocal parameter). P-V is Peak to Valley, which is twice the amplitude, measured in waves or OPD (Optical Path Difference). Note that these values are exemplary for a 7 um spot size. This value is exemplary and spot size is not limited to this value.

The embodiments described herein or portions thereof may be computer-implemented. The computer system may include a processor (e.g., a processor core, a microprocessor, a computing device, etc.), a main memory and a static memory, which communicate with each other via a bus. The machine may further include a display unit that may comprise a touch-screen, or a liquid crystal display (LCD), or a light emitting diode (LED) display, or a cathode ray tube (CRT). The computer system also may include a human input/output (I/O) device (e.g. a keyboard, an alphanumeric keypad, etc), a pointing device (e.g., a mouse, a touch screen, etc.), a drive unit (e.g., a disk drive unit, a CD/DVD drive, a tangible computer readable removable media drive, an SSD storage device, etc.), a signal generation device (e.g., a speaker, an audio output, etc), and a network interface device (e.g., an Ethernet interface, a wired network interface, a wireless network interface, a propagated signal interface, etc.).

The drive unit may include a machine-readable medium on which is stored a set of instructions (e.g., software, firmware, middleware, etc.) embodying any one, or all, of the methodologies described above. The set of instructions is also shown to reside, completely or at least partially, within the main memory and/or within the processor. The set of instructions may further be transmitted or received via the network interface device over the network bus.

It is to be understood that embodiments of this invention may be used as, or to support, a set of instructions executed upon some form of processing core (such as the CPU of a computer) or otherwise implemented or realized upon or within a machine- or computer-readable medium. A machine-readable medium includes any mechanism for storing or transmitting information in a form readable by a machine (e.g. a computer). For example, a machine-readable medium includes read-only memory (ROM); random access memory (RAM); magnetic disk storage media; optical storage media; flash memory devices; electrical, optical, acoustical or other form of propagated signals (e.g. carrier waves, infrared signals, digital signals, etc.); or any other type of media suitable for storing or transmitting information.

Figure 3B:
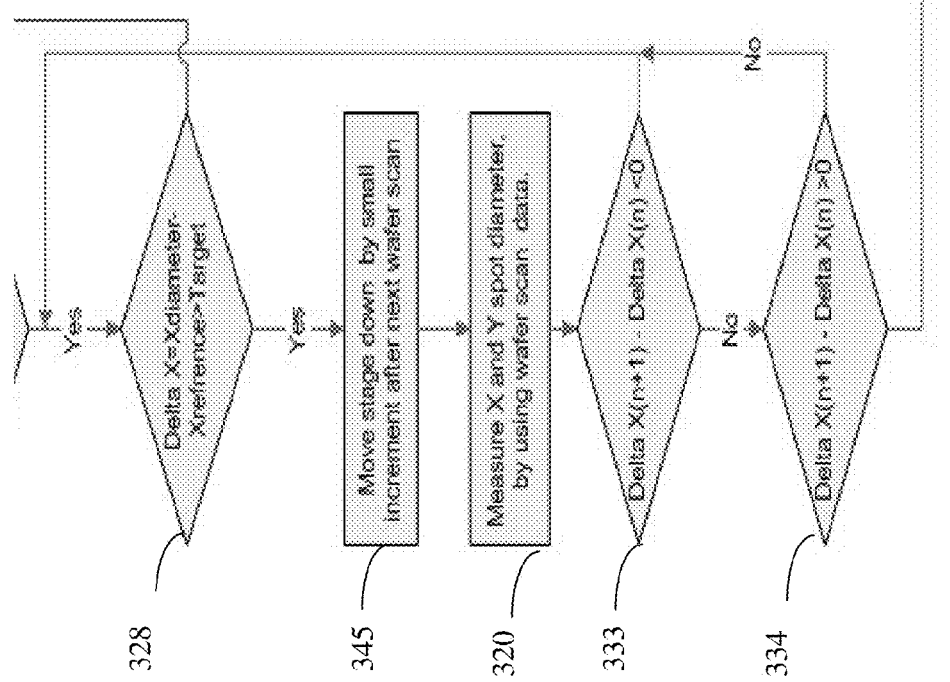

The apparatus and method embodiments herein enable automatic correction of laser beam waist position drift (coarse correction) and astigmatism (fine correction). The flow chart of FIG. 3 describes the decision process, including the possible employment of the astigmatism corrector. An inventive astigmatism corrector is disclosed: an extremely flexible design for a variable astigmatism correction system is provided which can be made from readily available interferometer transmission flats of very high quality. The inventive design does not require having a fixed reference to locate the x- and y-astigmatic waists with respect to, it only requires having a relative distance measurement between both waists, and can be adjusted "live" using the wafer inspection system's own built-in measurement capability. The apparatus and method embodiments disclosed herein provide a closed loop feedback arrangement in which laser beam astigmatism can be corrected to maintain beam quality even when the crystal ages. An astigmatism corrector, which may be as in the disclosed inventive corrector or may be an available corrector, is motorized and automated with a feedback and control system. The system allows measurement of astigmatism at the wafer surface, then uses that measurement in a feedback loop for correcting astigmatism. The result is that the laser beam spot does not change its characteristics for an extended time period, thus providing substantial extension of laser lifetime.

The apparatus and method embodiments disclosed herein can be utilized to minimize frequent and costly servicing of the laser tool, calibrations, realignment, spot size change, switching the spot where the laser light impinges on the crystal, i.e. rotating or otherwise moving the crystal, or early replacement of lasers.

It is not expected that the invention be limited to the exact embodiments disclosed herein. Those skilled in the art will recognize that changes and modifications can be made without departing from the inventive concept. By way of example, the system could include two astigmatism correctors, one for the xz plane, and the other for the yz plane. In this case the z stage would not be necessary for beam waist position correction. The scope of the invention may be construed in view of the claims.

With this in mind, we claim:

1. An apparatus for automatic correction of laser beam waist position drift in real time comprising:
  a DUV laser illumination source for illuminating a spot on a surface of a wafer, said wafer held on a wafer chuck; said laser illumination source providing an illumination laser beam traversing beam forming optics and having at least one beam waist Z position, said spot on said wafer surface having a spot size;
  a z-stage for translating said wafer on said wafer chuck in a Z direction;
  at least one astigmatism corrector to correct astigmatism in said illumination laser beam;
  means for measuring spot defocusing in X and Y beam directions; and an Image/Data processing Computer (IDC) including a controller for controlling said z-stage and said beam forming optics.

2. The apparatus of claim 1, wherein said DUV laser illumination source includes a non-linear crystal frequency doubler.

3. The apparatus of claim 1 in a wafer scanning system, wherein said means for measuring spot defocusing in X and Y beam directions utilizes wafer scan data taken during normal wafer scan tool operation.

4. The apparatus of claim 1, wherein said astigmatism corrector is positioned external to said laser illumination source and is in a system illumination path.

5. The apparatus of claim 1, wherein said astigmatism corrector is positioned inside of said laser illumination source as an integral part of a laser assembly.

6. The apparatus of claim 1, wherein said at least one astigmatism corrector comprises two wedged plates of small wedge angle, made of high quality transparent material, mounted in a system illumination path, said wedges pointing in opposite directions, said wedges having adjustable tilt angles;

said wedges mounted in a configuration to be adjustable to compensate for astigmatism in said illumination laser beam.

7. The apparatus of claim 1, wherein said at least one astigmatism corrector comprises two astigmatism correctors configured to correct said beam waist Z position in orthogonal planes.

8. An astigmatism corrector for correcting astigmatism in an illumination laser beam, comprising:

two wedged plates of small wedge angle, made of high quality transparent material, mounted in a system illumination path, said wedges pointing in opposite directions, said wedges having adjustable tilt angles;

said wedges mounted in a configuration to be adjustable to compensate for astigmatism in said illumination laser beam.

* * * * *